United States Patent [19]

Zehner et al.

[11] 4,041,068

[45] Aug. 9, 1977

[54] SYNTHESIS OF OXALATE ESTERS BY CATALYTIC OXIDATIVE CARBONYLATION OF BORATE ESTERS

[75] Inventors: Lee R. Zehner, Media; John G. Zajacek, Devon, both of Pa.

[73] Assignee: Atlantic Richfield Company, Los Angeles, Calif.

[21] Appl. No.: 700,947

[22] Filed: June 29, 1976

[51] Int. Cl.$^2$ .............................................. C07C 69/36
[52] U.S. Cl. ........................... 260/485 R; 260/465.4; 260/485 J; 260/485 L; 260/485 P
[58] Field of Search ........... 260/485 R, 485 L, 485 P, 260/485 H, 485 J, 465.4

[56] References Cited

U.S. PATENT DOCUMENTS 3,393,136   7/1968   Fenton et al. .................. 260/485 R

FOREIGN PATENT DOCUMENTS 2,213,435   10/1973   Germany .......................... 260/485

2,514,685   10/1975   Germany .......................... 260/485

OTHER PUBLICATIONS

Fenton, et al., J. Org. Chem. 39, No. 5, pp. 701–704, (1974).

Primary Examiner—Jane S. Myers
Attorney, Agent, or Firm—Delbert E. McCaslin

[57] ABSTRACT

A process for the preparation of oxalate esters by the catalytic oxidative carbonylation of orthoborate, metaborate and polyborate esters or mixtures thereof with carbon monoxide and oxygen or an oxygen-containing gas in the presence of a metal salt catalyst, an amine base and at least a catalytic amount of an alcohol. Preferably a catalytic amount of particular metal oxidizing salts are employed along with a catalytic amount of an amine salt compound which may be formed in situ by the addition of an acid. Alternatively various counterions and ligands of the metal salt catalysts may be employed.

27 Claims, No Drawings

SYNTHESIS OF OXALATE ESTERS BY CATALYTIC OXIDATIVE CARBONYLATION OF BORATE ESTERS

BACKGROUND OF THE INVENTION

A number of prior art processes have been proposed for the preparation of oxalate esters by the oxidative carbonylation of alcohols in the presence of metal salt catalysts, dehydrating agents, ferric or cupric redox agents in solution and various reaction accelerators.

The present invention is directed to a process for the preparation of oxalate esters while avoiding the problems associated with the prior art processes of carbonylating alcohols to obtain the desired oxalate ester. More particularly, the present process relates to the synthesis of oxalates by reacting carbon monoxide and oxygen with an orthoborate ester under elevated temperature and pressure conditions in the presence of a catalytic amount of a palladium, platinum, or rhodium salt catalyst and at least a catalytic amount of an amine base, and an alcohol and includes the employment of catalytic amounts of copper (II) or iron (III) oxidant salts in addition to catalytic amounts of an ammonium or substituted ammonium salt compound and ligands of the metal salt catalysts.

U.S. Pat. No 3,393,136 describes a process for the preparation of oxalates by contacting carbon monoxide at superatmospheric pressure, with a saturated monohydric alcohol solution of a platinum group metal salt and a soluble ferric or cupric salt (redox agent) while maintaining the salts in a highly oxidized state by the simultaneous introduction of oxygen or the application of a direct current electrical potential to the reaction zone. When oxygen is employed, explosive mixtures of oxygen and combustible organic vapors in the gas phase must be avoided and water scavengers or dehydrating agents such as alkyl orthoformic acid esters must be added to the liqid phase to prevent the accumulation of water.

In a recent article by Donald M. Fenton and Paul J. Steinward, Journal of Organic Chemistry, Vol. 39, No. 5, 1974, pp. 701–704, a general mechanism for the oxidative carbonylation of alcohols to yield dialkyl oxalates using a palladium redox system, oxygen and dehydrating agents has been proposed. In the absence of the necessary dehydrating agent, a large amount of carbon dioxide is formed and oxalatees are not produced. The necessity of the iron or copper redox system during the oxalate synthesis is emphasized.

A recent West German Pat. No. 2,213,435 discloses a method for the synthesis of oxalic acid and oxalate esters in water and alcohol respectively. A platinum group metal salt, a salt of a metal more electropositive than the platinum group metal, e.g. copper (II) chloride and an alkali metal salt comprise the catalyst. Oxygen in stoichiometric amounts was employed as the oxidant. A disadvantage of such reaction is that explosive mixtures of oxygen and carbon monoxide are necessary to effect reaction. Under non-explosive conditions only trace amounts of oxalate can be obtained.

A more recent West German Patent Publication No. 2,514,685 discloses a process for the preparation of dialkyl oxalates by reacting an aliphatic alcohol with carbon monoxide and oxygen under pressure in the presence of a catalyst of a mixture of a salt of a metal from the platinum group and a salt of copper or iron and a reaction accelerator including nitrates, sulfates, bicarbonates, carbonates, tertiary amines and hydroxides and carbonates of alkali metals and alkaline earth metals, pyridine, quinoline, urea and thiourea. Alcohol conversions are low.

The oxalate products of this invention may be employed, for example, as cellulose ether or ester and resin solvents, as dye intermediates and in the preparation of pharmaceuticals.

The process of the present invention provides a method of carrying out the oxidative carbonylation of orthoborate esters to produce an oxalate ester essentially without the coproduction of water which acts to poison the catalyst system and which even in small amounts also causes the production of large quantities of carbon dioxide and an attendant loss of the desired oxalate ester. Thus, by the process of the present invention, only small concentrations of water can accumulate in the reaction system since by the mechanism of the reaction any water which might be formed is rapidly consumed upon formation of coproduct boroxines or polyborate compounds. In addition, the coproduction of carbonate esters associated with such carbonylation reactions are minimized giving excellent selectivities to oxalate esters with high conversions of the borate ester. The boroxine or polyborate ester coproduced with the desired oxalate ester by the oxidative carbonylation reaction of the orthoborate ester may be readily separated from the desired oxalate and converted back to the respective reactant.

Other advantages of the present invention, as compared to known prior art processes for the production of oxalates are (1) elimination of hazardous operational conditions by avoiding exposive mixtures of oxygen and carbon monoxide, (2) avoiding the use of large amounts of corrosive chloride ions and (3) the ease of recovery and regeneration of the metal salt catalysts for reuse in the process.

SUMMARY OF THE INVENTION

According to the present invention there is provided a catalytic oxidative carbonylation process for the preparation of oxalate esters by reacting at least stoichiometric quantities of carbon monoxide and oxygen with an orthoborate ester, which process is carried out at elevated temperatures and pressures in the presence of a metal salt catalyst and a catalytic amount of an amine base and an alcohol and under relatively anhydrous conditions. The process of the invention also preferably employs, in catalytic amounts, particular metal oxidant salts and an acid or an ammonium or substituted ammonium salt compound to provide a pronounced effect on oxalate ester selectivity, and high conversions to the oxalates over the carbonates which may be present in only trace amounts. In addition, it has been found that alternatively catalytic amounts of various ligands, which will not work in themselves, may be used as co-catalysts in conjunction with the metal salt catalysts, the amines, the amine salts and the oxidant salts.

it is a primary object of this invention to provide a process for the preparation of oxalate esters while avoiding operational problems associated with prior processes.

It is another object of this invention to provide a novel reaction system useful in the conversion of carbon monoxide, oxygen, and orthoborate esters to oxalate esters.

It is a further object of this invention to provide a specific mechanism for the employment of catalysts, oxidant salts, amine salts and amines in an oxidative carbonylation process employing orthoborate esters as reactants.

These and other objects and advantages of this invention will become apparent from the description of the invention which follows and from the claims.

DESCRIPTION OF THE INVENTION

In accordance with the invention, an oxalate ester is produced by reacting, under relatively anhydrous liquid phase conditions, an orthoborate ester with carbon monoxide and oxygen at elevated temperatures and pressures in the presence of a catalyst comprising a palladium, rhodium or platinum metal salt or mixtures thereof, with or without a ligand such as lithium iodide as a co-catalyst, and in catalytic amounts, a base of a primary, secondary or tertiary amine, and an alcohol an preferably, in catalytic amounts, a copper (II) or iron (III) metal oxidant salt, an ammonium salt or amine salt or acid stronger than water which will not complex too strongly with the metal salt catalyst. The synthesis of the oxalate esters is carried out according to the following postulated equation

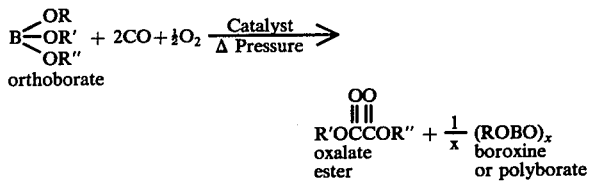

wherein R, R' and R" are substituted or unsubstituted alkyl or aralkyl groups. R, R' and R" may be the same or different and may contain other sustituents such as amido, alkoxy, amino, carboxy, cyano, etc. radicals. The substituents, in general, do not interfere with the reaction of the invention. Boroxines having the formula

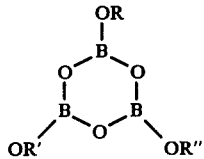

and polyborates having the formula $(ROBO)_3 \cdot X B_2O_3$ may also be employed as reactants either alone or in admixture with the orthoborates to produce oxalate esters by the process of the invention.

As indicated above, catalytic amounts of an amine as a base, and an alcohol are added to the reaction mixture and preferably in addition in catalytic amounts a metal oxidant salt and an amine salt. The amine salt so added may also be formed in situ in the reaction mixture by the addition of an acid such as sulfuric acid in order to form the necessary quantity of amine salt. Thus, for example, triethylamine can be employed initially in sufficient amounts and sulfuric acid added to form triethylammonium sulfate in the desired catalytic quantities. The addition of the amine salt helps to maintain the proton acidity of the reaction system.

The reaction between the orthoborate ester, carbon monoxide and oxygen may be carried out in an autoclave or any other high pressure reactor. Although the order of addition of reactants and other components may vary, a general procedure is to charge the orthoborate ester, amine, alcohol, amine salt (or the required amount of amine and acid), catalyst, and the oxidant salt into the reaction vessel, introduce the proper amount of carbon monoxide and oxygen to the desired reaction pressure and then heat the mixture to the desired temperature for the appropriate period. The reaction can be carried out batchwise or as a continuous process and the order of addition of the reactants may be varied to suit the particular apparatus employed. The reaction products are recovered and treated by any conventional method such as distillation and 1 or filtration, etc. to effect separation of the oxalate from unreacted materials, catalyst, oxidant salt, amine salt, by products, etc.

The orthoborate esters employed in at least stoichiometric quantities and suitable for use in the process of the present invention conform to the general formula

respectively as indicated hereinabove. R, R' and R" which may be the same or different may be substituted or unsubstituted alkyl or aralkyl groups preferably containing from 1 to 10 carbon atoms in the alkyl chain and from 1 to 2 aryl group substituents when R, R' and R" or all three is an aralkyl group. Particularly preferred are the orthoborates wherein R, R' and R" are straight chain alkyl groups containing from 1 to 8 carbon atoms such as triethyl borate.

Representative orthoborate esters suitable for use in this invention include, for example, trimethyl borate, triethyl borate, tri-2-chloroethyl borate, tritolyl borate, tri-methoxybenzyl borate, tri-chlorobenzyl borate, tri-benzyl borate, tri-4-butylphenyl borate, tri- n-propyl and tri-isopropyl borates, tri-(1,3-dichloro-2- propyl) borate, tri-n-butyl, tri-s-butyl and tri-t-butyl borates, tri-($\beta$, $\beta$, $\beta$-trichloro-t-butyl) borate, triphenyl borate, tri-o-chlorophenyl borate, tri-n-amyl borate, tri-t-amyl borate, tri-(o-phenylphenyl) borate, tri-n- hexyl borate, tri-3-heptyl borate, tri-3-pentyl borate, tri-n-octyl and tri-isooctyl borates, tri-(2-ethylhexyl) borate, tri-(methylisobutylcarbinyl) borate, tri-(diisobutylcarbinyl) borate, tri-(2,5-dimethylbenzyl) borate, etc.

The alcohols employed in catalytic quantities and suitable for use in the process of the present invention can be monohydric saturated aliphatic and alicyclic alcohols or aromatic alcohols and may contain other substituents such as amido, alkoxy, amino, carboxy, cyano, etc. radicals in addition to the hydroxyl group. The sustituents, in general, do not interfere with the reaction of the invention.

The alcohols which may be employed in concentrations of from 0.1 to 50 weight percent preferably from 1 to 3 weight percent and which may be primary, secondary or tertiary alcohols conform to the general formula ROH, wherein R is an optionally substituted aliphatic or alicyclic group containing from 1 to 20 carbon atoms and preferably unsubstituted aliphatic alcohols containing from 1 to 8 carbon atoms. R may also be an aromatic group containing one or more benzenoid rings preferably not more than 3 rings which may be fused or joined by single valency bonds, directly or through bridging groups which may be, for example, oxygen or sulfur atoms or sulfoxide, sulfone or carbonyl groups or alkylene groups in which, if desired, the carbon chain may be interrupted by, for example, oxygen or sulfur atoms, sulfoxide, sulfone or carbonyl groups, for example methylene, oxymethylene, dimethylene sulfone or dimethylene ketone groups. Representative alcohols especially suitable for use in this invention are monohydric alcohols such as methyl, ethyl, n-, iso-, sec-, and tertbutyl, amyl, hexyl, octyl, lauryl, n- and iso-propyl, cetyl, benzyl, chlorobenzyl and methoxy-benzyl alcohols as well as, for example cyclohexanol, octanols, heptanols, decanols, undecanols, 2-ethyl hexanol, nonanol, myristyl alcohol, stearyl alcohol, methyl cyclohexanol, pentadecanol, oleyl and eicosonyl alcohols, and the like. The preferred alcohols are the primary and secondary monohydric alcohols, such as methanol, ethanol and 1- and 2-propanol, n-butyl alcohol etc. up to 8 carbon atoms.

The amines employed in catalytic quantities in the process of the invention, used as a base, may be primary, secondary or tertiary amines and include aliphatic, cycloaliphatic, aromatic and heterocyclic amines or mixtures thereof. The amines may be unsubstituted or contain other substituents such as halides, alkyl, aryl, hydroxy, amino, alkylamino, carboxy, etc. The amines may be employed in the reaction in concentrations of from 0.1 to 5 weight percent and preferably at a concentration ∼3 weight percent.

Representative amines as hereinabove described, include for example, mono-, di- and tri-methyl, ethyl and propyl amines, iso- and diisopropylamines, allyl amines, mono-, di-, tri-, iso and diisobutyl amines, 1- methylpropyl amine, 1,1-dimethylethyl amine, amyl amines, cyclohexyl amine, dicyclohexylamine, 1,3-dimethyl-butyl amine, 2-ethylhexamine, 1-cyclopentyl-2-amino propane, 1,1,3-tetramethylbutylamine, aniline, ethylene diamine, methylene diamines, ethanolamine, octylamines, n-decylamine, do-, tetra-, hexa-, octa-, dido-, ditetra-, diocta-, trido- and triocta-decylamines, chloro-anilines, nitro-anilines, toluidines, naphthylamine, N-methyl and N-ethyl and N,N-dimethyl and N,N-diethyl aniline, di- and tri- phenylamines, N,N-diamylaniline, benzyl dimethyl amine, piperidine, pyrrolidine, etc. The preferred amines used as bases are the tertiary amines such as triethylamine.

The metal salt catalysts which may be employed in the process of this invention are the palladium, platinum and rhodium salts. Among the chemical forms of the metal compounds which can be used are the palladium, platinum and rhodium, halides, sulfates, oxalates and acetates preferably the palladium (II) halides such as palladium (II) chloride and palladium (II) iodide. Representative catalytic metal salt compounds include, for example palladium (II) chloride, rhodium (III) chloride, palladium (II) sulfate, palladium (II) oxalate, palladium (II) acetate, palladium (II) iodide, rhodium (III) bromide, platinum (II) chloride, platinum (II) sulfate, etc.

The catalysts employed may be in a homogeneous state in the reaction mixture at reaction conditions. Thus, the catalysts may be present in solution, or suspension and may also be on support materials such as alumina, silica gel, aluminosilicates, activated carbon or zeolites.

The reaction is generally carried out in the presence of a catalytic proportion of the metal salt catalyst and will proceed with small amounts of the metal salt catalyst compounds hereinabove described. Generally the proportions of the metal salt catalyst used in the reaction will be equivalent to between about 0.001 to 5 weight percent of the orthoborate employed and are preferably employed in amounts between about 0.01 to 2 percent by weight of the orthoborate employed. Larger or smaller amounts may be employed at varied pressures and temperatures.

As mentioned hereinabove, a ligand or coordination complex compound of the metal catalyst may be employed in the process of the invention as a co-catalyst and thereby also achieve a pronounced increase in the selectivity for the oxalate ester. The ligands may be, for example, alkyl or aryl phosphines, arsines, iodides or stibines. The complexes of the metal catalysts which are suitable as co-catalysts in the process of the present invention include complex compounds of palladium, platinum and rhodium. The complex compounds may contain one or more atoms of the said metals in the molecule and when more than one such atom is present, the metals may be the same or different. The mono- or poly-dentate ligands which are present in the molecule of the complex compounds and in which at least one of the electron-donating atoms is an atom of phosphorous, arsenic or antimony or an iodide ion containing a lone pair of electrons may be, for example, organo-phosphines, -iodides, -arsines and -stibines. Suitable mono-dentate ligands include alkyl phosphines such as trimethylphosphine and tributylphosphine, aryl-phosphines such as diethylphenyl-phosphine and radicals derived from such phosphines, for example the radical having the formula — $P(CH_3)_2$. Hydrocarbyloxy phosphines, i.e., phosphites, such as triphenyl phosphite may also be employed. Suitable polydentate ligands include tetramethyl diphosphinoethane adnd tetraphenyl di-phosphinoethane. Exactly analogous derivatives of arsenic and antimony may be used; however, because of their greater ease of preparation and stability of the derived complexes, the hydrocarbyl derivatives of phosphorus are preferred. It is also preferred to employ alkali metal iodides, e.g. lithium iodide.

The complex compounds suitable for use in the process of the present invention may contain in the molecule, in addition to the ligands discussed above, one or more other atoms, groups or molecules, which are chemically bonded to the metal atom or atoms. Atoms which may be bonded to the metal include, for example, hydrogen, nitrogen and halogen atoms; groups which may be bonded to the metal include, for example hydrocarbyl, hydrocarbyloxy, carbonyl, nitrosyl, cyano and $SnCl_3$— groups; molecules which may be bonded to the metal include, for example, organic isocyanides and isothiocyanates.

Examples of suitable complex compounds are those represented by the following formulae:

| | |
|---|---|
| $RhBr_3(PPhEt_2)_3$ | $Rh(CO)Cl(AsEt_3)_2$ |
| $RhCl(CO)(PPhEt_2)_2$ | $RhCl(CO)(PEt_3)_2$ |
| $Rh(Ph_2PCH_2CH_2PPH_2)_2Cl$ | $PdCl_2(PPh_3)_2$ |
| $Rh[(PhO)_3PI_3Cl$ | $Li_2PdI_4$ |
| $PdI_2(PPh_3)_2$ | $PtCl_2(p\text{-}ClC_6H_4Pn\text{-}Bu_2)_2$ |

The complex compounds employed may be introduced into the reaction mixture as such, or they may be formed in situ from a suitable metal compound noted above and the desired ligand.

The ligand or complex compounds may be used in catalytic amounts of from 0 to 3 percent preferably from 0.1 to 1 percent by weight of the orthoborate ester to be reacted although larger or smaller amounts may be employed at varied pressures or reaction rates.

The oxidizing salts which may be employed in an anhydrous condition and in catalytic amounts of from 0 to 10 weight percent preferably 3 to 5 weight percent in the process of the invention include the copper (II) salts such as the sulfates, trifluoroacetates, oxalates, or acetates preferably the copper (II) sulfates and trifluoroacetates. Representative oxidant salts include, for example, copper (II) sulfate, copper (II) trifluoroacetate, copper (II) acetate, copper (II) oxalate, copper (II) triflate and copper (II) fluorosulfonate. Excess halides are detrimental to the reaction system of the present invention.

The amine salts which are employed in an anhydrous condition and in a catalytic amount of from 0 to 10 weight percent preferably in a concentration ~ 10 weight percent in the process of the invention include, for example, the ammonium and substituted ammonium sulfates, trifluoroacetates, and acetates, preferably the tertiary amine sulfates such as triethyl ammonium sulfate. Representative amine salts include, for example diethylammonium sulfate, ethylammonium sulfate, butylammonium sulfate, ammonium sulfate, trimethylammonium sulfate, mono-methylammonium sulfate, trimethyl ammonium hydrogen sulfate, ammonium acetate, ammonium trifluoroacetate, methyl-, ethyl- and butylammoniumtrifluoroacetate, etc.

The amine salts may be added as such or formed in situ in the required amounts upon the addition of an acid, such as, sulfuric, benzene sulfonic, phosphoric, o-boric, p-toluene sulfonic, acetic or trifluoroacetic, to the reaction mixture while using greater than the required quantities of the amine base. The acids which may be used to form the salt include those which do not form a complex with the metal salt catalyst or when employed the metal salt oxidant compounds inactivating the catalyst and oxidant. As indicated hereinabove the acids must be of sufficient strength, i.e., stronger than water, and such that the anion will not complex with the metal catalyst or oxidant salt. The salts which may be formed in situ may in themselves not necessarily be isolable and may exist in equilibrium in the reaction mixture under carbonylation reaction conditions. Thus, such salts could not be added per se but, as indicated above may be formed in situ upon the addition of a suitable acid to the reaction mixture containing amine.

Although not required, solvents, if desired, which are chemically inert to the components of the reaction system may be employed. Suitable solvents include, for example, organic esters such as ethyl acetate, n-propyl formate, isopropyl acetate, sec- and iso-butyl acetate, amyl acetate, cyclohexyl acetate, n-propyl benzoate, lower alkyl phthalates, etc. and the alkyl sulfones and sulfoxides such as propyl ethyl sulfoxide, diisopropyl sulfone, diisooctyl sulfoxide, acetone, cyclohexanone, methyl formate, as well as N,N-dimethylformamide, etc.

As indicated above the reaction can be suitably performed by introducing the oxygen and carbon monoxide at a desired pressure into contact with the orthoborate ester reaction medium containing the specified reactants, catalyst, alcohol and amine and preferably an amine salt and oxidant salt and heating to the desired temperature. In general, a carbon monoxide pressure of about 500 psi to about 3000 psi partial pressure and preferably from 900 psi to about 2200 psi is employed. Stoichiometric quantities of carbon monoxide are generally employed. However, an excess of carbon monoxide may be employed, for example, in continuous processes where a large excess of or high carbon monoxide requirements are generally utilized, a suitable recycle of the carbon monoxide may be employed. The reaction will proceed at temperatures of from about 50° C. to 200° C. It is generally preferred to operate the process at temperatures in the range of 100° C. to 135° C. to obtain a convenient rate of reaction. Heating and/or cooling means may be employed interior and/or exterior of the reaction to maintain the temperature within the desired range.

At least stoichiometric amounts of oxygen or an oxygen containing gas such as air are generally employed and at any oxygen partial pressure such that the explosive range is avoided. Thus, the concentrations of oxygen should be low enough so that the reaction mixture is not potentially explosive. The Handbook of Chemistry and Physics, 48th Edition, 1967 indicates that the explosive limits of pure oxygen in carbon monoxide is 6.1 to 84.5 volume percent and air in carbon monoxide to be 25.8 to 87.5 volume percent.

The reaction time is generally dependent upon the orthoborate ester being reacted, temperature, pressure and on the amount and type of catalyst being charged as well as the type of equipment being employed. Reaction times will vary dependent on whether the process is continuous or batch.

The following examples are provided to illustrate the invention in accordance with the principles of this invention but are not to be construed as limiting the invention in any way except as indicated by the appended claims.

In the Examples which follow the reactions were run in a 300 ml stainless steel stirred autoclave. The liquid and solid materials were charged to the reactor (as solutions whenever possible). At least 1000 psi CO was charged to the reactor, which was heated to reaction temperature. The pressure was increased to the desired value by adding more CO. Oxygen was added in such an amount that a potentially explosive gas mixture was never obtained in the reactor. Enough CO was employed to sweep the oxygen out of the entire length of the tubing and into the reactor. The ensueing rate of gas uptake was allowed to level off before the next addition of CO or oxygen. Additional CO was charged to maintain constant pressure. When an exotherm was observed, cold water was circulated through the internal cooling coil to maintain the reaction temperature within ±5° C. The process of charging oxygen and sweeping out the line with CO was repeated until no more gas uptake was observed. The reactor was cooled to ambient temperature. A gas sample was obtained, and the composition was determined by mass spectral analysis. The liquid product was analyzed by gas-liquid phase chromatography (glc) for the oxalate and carbonate ester.

EXAMPLE I

A solution of 0.19 g. lithium iodide (1.41 mmoles), 2.34 g. triethylamine (23.0 mmoles), 6.96 g. triethylammonium sulfate (23.0 mmoles), 50.7 g. methanol (1584 mmoles), and 55ml trimethyl borate (0.53 mole) was charged to the autoclave along with 0.25 g. palladium (II) iodide (0.69 mmole) and 3.70 g. anhydrous copper (II) sulfate (23.0 mmoles). The reaction temperature was 100° C. The total initial pressure at reaction temperature was 1500 psi. 100 psi oxygen was charged followed by 200 psi CO. A rapid pressure drop was noted in addition to a strong exotherm. 200 psi CO was added to bring the total pressure back up above 1500 psi. The oxygen/CO charge cycle was repeated five more times. Total oxygen consumed was 634 psi. A total of 1600 psi pressure drop was observed over a reaction time of approximately 3.8 hours. The total pressure ranged between 1500 and 2125 psi during reaction Glc analysis showed the presence of a boroxine and methanol but no trimethyl borate was detectable. The liquid reaction product contained 0.29 mole dimethyl oxalate and no dimethyl carbonate according to glc analysis. 0.8 mole of $CO_2$ was detected in the gaseous product.

EXAMPLE II

The same amounts of materials as in Example I with the exception that the triethylammonium sulfate was replaced by 0.95 g. boric acid (15.4 mmoles) were charged to the autoclave. The reaction temperature was 100° C. The total initial pressure was 1400 psi at reaction temperature. 65 psi oxygen was charged followed by 200 psi CO. A strong exotherm and rapid pressure drop were noted. The oxygen/CO charge cycle was repeated ten more times. Total oxygen consumed was 1212 psi. A total of 2205 psi pressure drop was observed during the reaction period of (7.0 hours). The total pressure ranged between 1400 and 2245 psi during the reaction. Glc analysis of the liquid showed the presence of methanol, and dimethoxymethane. Trimethyl borate was not detectible. The liquid reaction product contained 0.28 mole of dimethyl oxalate and a trace of dimethyl carbonate according to quantitative glc analysis. 0.26 mole of $CO_2$ was detected in the gaseous product.

EXAMPLE III

A solution of 2.34 g. triethylamine (23.0 mmoles), 6.96 g. triethylammonium sulfate (23.0 mmoles), 10.0 g. methanol (321 mmoles), and 55 ml trimethyl borate (0.616 mole) along with 0.65 mole of N,N-dimethylformamide was charged to the autoclave. 0.25 g. palladium (II) iodide (0.69 mmoles), 0.19 g. lithium iodide (1.41 mmoles) and 3.70 g. anhydrous copper (II) sulfate (23.0 mmoles were charged separately as solids. The reaction temperature was 125° C. The total initial pressure at reaction temperature was 1480 psi. 100 psi oxygen was charged followed buy 200 psi CO. A rapid pressure drop was observed along with a large exotherm. An additional 100 psi CO was charged in order to raise the total pressure above 1500 psi. The oxygen/CO charge cycle was repeated five more times using between 200 and 300 psi CO after each 100 psi charge of oxygen. A total of 2325 psi pressure drop was observed over a reaction time of approximately 5.8 hours. The total pressure ranged between 1480 and 2050 psi during the reaction. The only products detectible by glc were dimethoxymethane, a boroxine, and dimethyl oxalate. Some methanol and triethylamine were detected, but unreacted trimethyl borate could not be detected. The liquid reaction product contained 0.17 mole of dimethyl oxalate and no dimethyl carbonate according to quantitative glc analysis. 0.16 mole of $CO_2$ was detected in the gaseous product.

EXAMPLE IV

A solution of 2.34 g. triethylamine (23.0 mmoles), 0.95 g. boric acid (15.3 mmoles), 3.0 g. ethanol (65 mmoles), and 60 ml triethyl borate (0.410 mole) and 0.387 mole of ,N-dimethylformamide was charged to the autoclave. The following solids were charged separately: 0.25 g. palladium (II) iodide (0.69 mmole), 0.19 g. lithium iodide (1.41 mmoles), and 4.60 g. iron (III) sulfate (11.5 mmoles). The reaction temperature and initial pressure were 100° C. and 1475 psi respectively. 100 psi oxygen followed by 200 psi CO was charged. A total of 1825 psi pressure drop was observed during a reaction period of 5.2 hours. The total pressure ranged between 1475 and 2025 psi during the reaction. Total oxygen consumed was 717 psi. Analysis of the reaction products showed 0.13 mole of diethyl oxalate, a trace (< .005 mole) diethyl carbonate and 0.17 mole of $CO_2$.

EXAMPLE V

A solution of 2.34 g. triethylamine (23.0 mmoles), 3.0 g. methanol (93.6 mmoles), and 55 ml trimethyl borate (0.616 mole) was charged to the autoclave along with 0.25 g. palladium (II) iodide (0.69 mmole), 0.19 g. lithium iodide (1.41 mmoles), 0.95 g. boric acid (15.4 mmoles), and 3.70 g. copper (II) sulfate (23.0 mmoles), The reaction temperature was 100° C. The total initial pressure at reaction temperature was 1500 psi. 100 psi oxygen was charged followed by 200 psi CO. An exotherm and rapid pressure drop were observed. The oxygen/CO charge cycle was repeated six more time using between 200 and 400 psi CO charges after each 100 psi charge of oxygen. A total of 2250 psi pressure drop was observed over a reaction time of approximately 5.3 hours. The total pressure ranged between 1460 and 2000 psi during reaction. Total oxygen consumed was 800 psi. Glc analysis showed the presence of a trace amount of dimethyl carbonate and 0.12 mole dimethyl oxalate. $CO_2$ (0.14 mole) was detected in the gaseous reaction product.

EXAMPLE VI

A solution of 2.34 g. triethylamine (23.0 mmoles), 6.9 g. butanol (93.6 mmoles), and 50 ml tri-n-butyl borate (0.218 mole) was charged to the autoclave. The solids charged were 0.25 g. palladium (II) iodide (0.69 mmole), 1.05 g. triphenylphosphine (4.0 mmoles) and 3.70 g. anhydrous copper (II) sulfate (23.0 mmoles). The reaction temperature was 110° C. The total initial pressure was 1500 psi. 100 psi oxygen was charged followed by 200 psi CO. A relatively small exotherm and a moderate rate of pressure drop were noted. The next oxygen/CO charges showed exotherms and faster rates of pressure drop. 200-300 psi CO charges were used after each 100 psi oxygen charge. A total of 2330 psi pressure drop was observed over a reaction time period of approximately 5.8 hours. The total pressure ranged between 1440 and 1865 psi during the reaction. According to quantitative glc analysis, the liquid reaction product contained 26.1 g. dibutyl oxalate and 6.1 g. dibutyl carbonate. The gaseous reaction product contained 1.58 g. $CO_2$.

EXAMPLE VII

A solution of 2.34 g. triethylamine (23.0 mmoles), 3.0 g. methanol (93.6 mmoles), and 55 ml trimethyl borate (0.53 mole) was charged to the autoclave along with the separate solid materials: 0.18 g. palladium (II) chloride (1.0 mmole), 0.19 g. lithium iodide (1.41 mmoles), 3.69 g. copper (II) oxalate hemihydrate (23.0 mmoles), and 6.96 g. triethylammonium sulfate (23.0 mmoles). The reaction temperature was 100° C. The total initial pressure was 1500 psi. 100 psi oxygen and 200 psi CO were charged to the autoclave. A strong exotherm and rapid pressure drop were noted. The same results were obtained for the next four oxygen/CO charges in which 200-300 psi CO was charged after each 100 psi oxygen charge. The sixth oxygen/CO charge showed no exotherm and a small pressure drop. The reaction mixture was maintained at temperature and pressure for 50 minutes after the last recorded pressure drop. A total of 1725 psi pressure drop was observed over a reaction time of approximately 4.6 hours. The total pressure ranged between 1425 and 1850 psi. Dimethyl oxalate (0.361 mole) was obtained. Dimethyl carbonate was detected in the liquid product.

EXAMPLE VIII

A solution of 9.27 g. tributylamine (50.0 mmoles), 76.9 g. methanol (2.4 moles), and 55 ml trimethyl borate (0.53 mole) along with 0.50 g. palladium (II) oxalate (2.6 mmole), 0.19 g. lithium iodide (1.41 mmoles) and 6.96 g. triethylammonium sulfate were charged to the autoclave. The reaction temperature was 125° C. The total initial pressure was 1500 psi at reaction temperature. 100 psi oxygen was charged followed by 200 psi CO. No gas uptake or exotherm was detected up to 15 minutes afterward. When the oxygen/CO charges was repeated, immediately a strong exotherm and rapid pressure drop were noted. The concentration of oxygen was such that the gas mixture was potentially explosive. Three more oxygen/CO charges were made, and again the reaction was initiated only when potentially explosive mistures of oxygen and CO were employed. The reaction was not run to completion. 1280 psi total pressure drop was recorded over a time period of approximately 7.7 hours. The total pressure ranged between 1480 and 2100 psi during the reaction. G1c analysis of the liquid product showed the presense of methanol, dimethyl carbonate, and unreacted trimethyl borate. The liquid contained dimethyl oxalate (0.23 mole). The gaseous product contained $CO_2$ (0.264 mole).

EXAMPLE IX

A solution of 5.06 g. triethylamine (50 mmoles), 1.72 g. (16.9 mmoles) of concentrated sulfuric acid (96.4 percent), 3.0 g. methanol (93.6 mmoles), and 55 ml trimethyl borate (0.53 mole) was charged to the autoclave along with 0.22 g. palladium (II) acetate (1.0 mmoles), 0.19 g. lithium iodide (1.41 mmoles), 3.69 g. copper (II) oxalate hemihydrate (23mmoles), and 1.58 g. oxalic acid dihydrate (12.5 mmoles). The reaction temperature was 135° c. The total initial pressure at reaction temperature was 1500 psi. Six 100 psi oxygen/200 psi CO charges were added to the autoclave over the period of 4.5 hours. Each addition of oxygen/CO showed a relatively slow pressure drop and no noticeable exothermic behavior. A total pressure drop of 1150 psi was recorded. The total pressure ranged between 1800 and 2240 psi during reaction. G1c analysis of the reaction product showed the presence of methanol, unreacted trimethyl borate, dimethyl carbonate, and 10.9 g. dimethyl oxalate (0.177 mole). 3.52 g. $CO_2$ (0.080 mole) was detected in the gaseous reaction product.

EXAMPLE X

A solution of 2.34 g. triethylamine (23.0 mmoles), 6.96 g. triethylammonium sulfate (23.0 mmoles), 1.4 g. ethanol (31.2 mmoles), 60 ml triethyl borate (0.410 mole) was charged to the autoclave along with 0.21 g. rhodium (III) chloride (1.0 mmoles) 0.19 g. lithium iodide (1.41 mmoles), and 9.4 g. copper (II) trifluoroacetate (32.4 mmoles). The reaction temperature was 100° c. The total initial pressure at reaction temperature was 1500 psi. 100 psi oxygen followed by 200 psi CO was charged. After the pressure levelled out, the oxygen/CO charge was repeated. A rapid uptake and strong exotherm were observed. The oxygen/CO charge was repeated six more times. A total of 2125 psi pressure drop was observed over a reaction time of approximately 6.8 hours. The total pressure ranged between 1475 and 2050 psi during reaction. Glc analysis of the recovered liquid product showed the presence of methanol, 7.5 g. diethyl carbonate (0.064 mole), and 57.5 g. diethyl oxalate (0.394 mole). No triethyl borate was detectible in the liquid product. The gaseous product contained 15.0 g. $CO_2$ (0.341 mole).

EXAMPLE XI

A solution of 7.02 g. triethylamine (69.4 mmoles), 1.18 g. concentrated sulfuric acid (11.6 mmoles), 1.0 g. absolute methanol (31.2 mmoles), and 55 ml trimethyl borate (0.53 mole) plus 0.25 g. palladium (II) sulfate (1.0 mmole), 0.19 g. lithium iodide (1.41 mmoles), and 3.70 g. anhydrous copper (II) sulfate (23.0 mmoles) were charged to the autoclave. The reaction temperature was 100° C. The total initial pressure at reactiom temperature was 1500 psi. 100 psi oxygen was charged followed by 200 psi CO. Another oxygen/CO charge was made. A total of 680 psi pressure drop was observed in a period of 2.7 hours. The reaction was not taken to completion. The total pressure during reaction was between 1420 and 1800 psi. The gaseous reaction product contained 6.2 g. $CO_2$ (0.14 mole). According to glc analysis, the reaction product contained some methanols, 16.3 g. dimethyl oxalate (0.138 mole), and 1.8 g. dimethyl carbonate (0.020 mole).

We claim

1. A process for the preparation of oxalate esters which comprises reacting under substantially anhydrous conditions in orthoborate ester having the formula

wherein R is alkyl or aralkyl groups which may contain substituents which do not interfere with the reaction, with carbon monoxide and oxygen at a pressure of between about 500 psi and 3000 psi and at a temperature in the range of about 50° C. to 200° C. in the presence of an effective amount of a catalyst selected from the group consisting of palladium, platinum and rhodium salt compounds and a catalytic amount of an aliphatic, cycloaliphatic, aromatic or heterocyclic amine, and a catalytic amount of a monohydric aliphatic, alicyclic or aromatic alcohol which may contain substituents which do not interfere with the reaction, and recovering the desired oxalate ester.

2. A process according to claim 1 wherein the catalyst salt compound is selected from the group consisting of palladium, platinum and rhodium, halides, oxalates, sulfates and acetates.

3. A process according to claim 2 wherein the catalyst is selected from palladium chloride, palladium iodide, palladium oxalate, palladium sulfate, palladium acetate, platinum chloride and rhodium chloride.

4. A process according to claim 3 wherein the catalyst is palladium iodide.

5. A process according to claim 1 wherein the amine is employed in concentrations of from 0.1 to 5 weight percent.

6. A process according to claim 5 wherein the amine is triethylamine.

7. A process according to claim 1 wherein the alcohol is employed in concentrations of from 0.1 to 50 weight percent.

8. A process according to claim 7 wherein the alcohol is selected from the group consisting of methyl alcohol and ethyl alcohol.

9. A process according to claim 8 wherein the alcohol is methyl alcohol.

10. A process according to claim 1 wherein the reaction is carried out in the presence of a catalytic amount of a copper (II) or iron (III) oxidant salt compound and an ammonium or substituted ammonium salt compound.

11. A process according to claim 10 wherein the oxidant salt compound is copper (II) or iron (III) oxalate, sulfate, acetate or trifluoroacetate.

12. A process according to claim 11 wherein the oxidant salt is copper (II) sulfate.

13. A process according to claim 11 wherein the oxidant salt is copper (II) oxalate.

14. A process according to claim 11 wherein the oxidant salt is iron (III) sulfate.

15. A process according to claim 10 wherein the ammonium salt compound is triethylammonium sulfate.

16. A process according to claim 10 wherein the ammonium or substituted ammonium salt compound is formed in situ upon the addition of an acid to the reaction mixture containing an excess of amine over the required quantities of amine base, said acid being of a strength stronger than water and such that the anion will not complex with the metal salt catalyst or metal oxidant salt compound.

17. A process according to claim 16 wherein said acid is sulfuric acid.

18. A process according to claim 16 wherein said acid is boric acid.

19. A process according to claim 1 wherein the reaction is carried out in the presence of a cocatalytic amount of an organic mono- or poly-dentate ligand or co-ordination complex of the metal catalyst selected from the group consisting of alkyl, aryl and halogen substituted phosphines, arsines, stibines and iodides.

20. A process according to claim 19 wherein the ligand or co-ordination complex is lithium iodide.

21. A process according to claim 1 wherein the pressure is between about 900 psi and 2200 psi and the temperature is in the range of about 100° C. to 135° C.

22. A process according to claim 21 wherein the orthoborate ester is trimethyl borate, the catalyst is palladium iodide, the amine is triethylamine and the alcohol is methyl alcohol.

23. A process according to claim 22 wherein a catalytic amount of a copper (II) sulfate, triethyl ammonium sulfate and lithium iodide is added to the reaction mixture.

24. A process according to claim 21 wherein the orthoborate ester is triethyl borate, the catalyst is palladium iodide, the amine is triethylamine and the alcohol is ethyl alcohol.

25. A process according to claim 24 wherein a catalytic amount of a copper (II) sulfate, boric acid, and lithium iodide is added to reaction mixture.

26. A process according to claim 1 wherein an oxygen-containing gas is employed as a source of oxygen for the reaction.

27. A process according to claim 1 wherein the catalyst is supported.

* * * * *